United States Patent [19]

Stotts et al.

[11] Patent Number: 5,545,182
[45] Date of Patent: Aug. 13, 1996

[54] CARDIOVERTER/DEFIBRILLATOR SHOCK TIMING FUNCTION

[75] Inventors: Lawrence J. Stotts, Lake Jackson, Tex.; Eckhard Alt, Ottobrunn, Germany

[73] Assignee: Intermedics, Inc., Angleton, Tex.

[21] Appl. No.: 310,281

[22] Filed: Sep. 21, 1994

[51] Int. Cl.$^6$ .................................. A61N 1/39; A61N 1/36
[52] U.S. Cl. .................................. 607/5; 607/4; 607/6
[58] Field of Search ............................ 607/4, 5, 6, 16

[56] References Cited

U.S. PATENT DOCUMENTS

| | | | |
|---|---|---|---|
| 4,475,551 | 10/1984 | Langer et al. | 607/5 |
| 4,559,946 | 12/1985 | Mower | 607/5 |
| 4,880,004 | 11/1989 | Baker, Jr. et at. | 607/5 |
| 5,117,824 | 6/1992 | Keimel et al. | 607/4 |
| 5,179,945 | 1/1993 | Van Hofwegen et al. | 607/5 |
| 5,184,615 | 2/1993 | Nappholz et al. | 607/4 |
| 5,279,291 | 1/1994 | Adams et al. | 607/5 |
| 5,350,401 | 9/1994 | Levine | 607/4 |
| 5,431,685 | 7/1995 | Alt | 607/6 |

Primary Examiner—William E. Kamm
Assistant Examiner—Carl H. Layno
Attorney, Agent, or Firm—Wigman, Cohen, Leitner & Myers, P.C.

[57] ABSTRACT

An implantable automatic cardioverter/defibrillator device for a cardiac patient is automatically responsive to sensing of electrical cardiac activity of the heart of a patient in which the device is implanted for detection and treatment of fibrillation. A prescribed electrical shock waveform regimen is generated as electrical defibrillation therapy for application to the heart in response to detection of fibrillation of the heart. A timing function circuit responds to the detection by timing the delivery of the generated prescribed electrical waveform regimen to be applied at a point in time at which the fibrillation ECG has substantially its highest amplitude and lowest frequency, as a point of high susceptibility to reversion to sinus rhythm upon application of a shock, and with low defibfillation threshold, to enhance the probability of successful defibrillation, and to synchronize the shock delivery to this sensed intracardiac event.

11 Claims, 2 Drawing Sheets

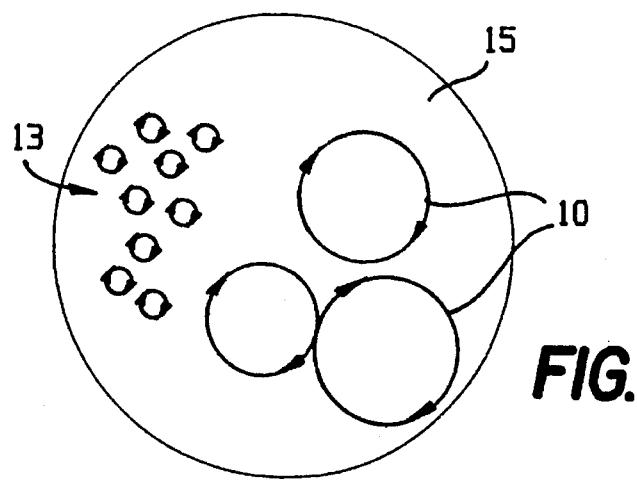
FIG. 1
FIG. 3 (PRIOR ART)
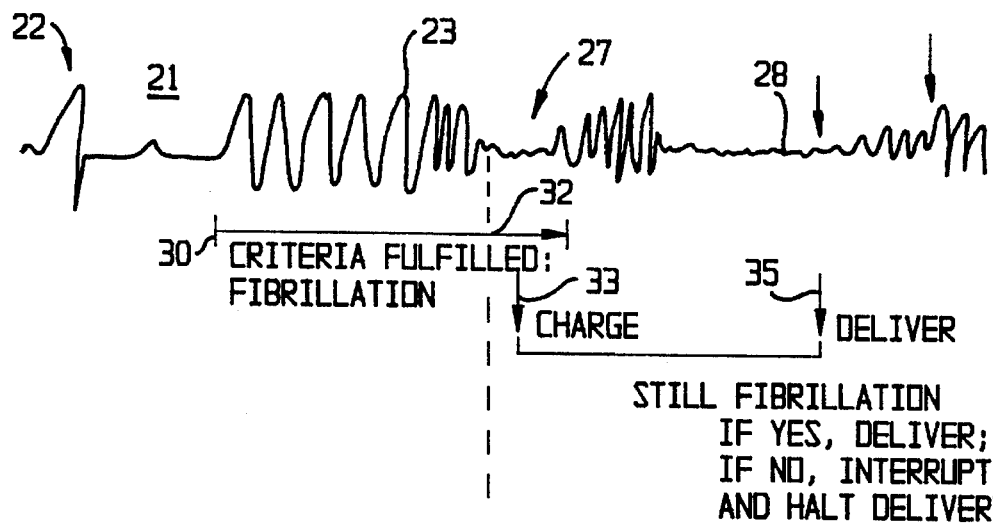
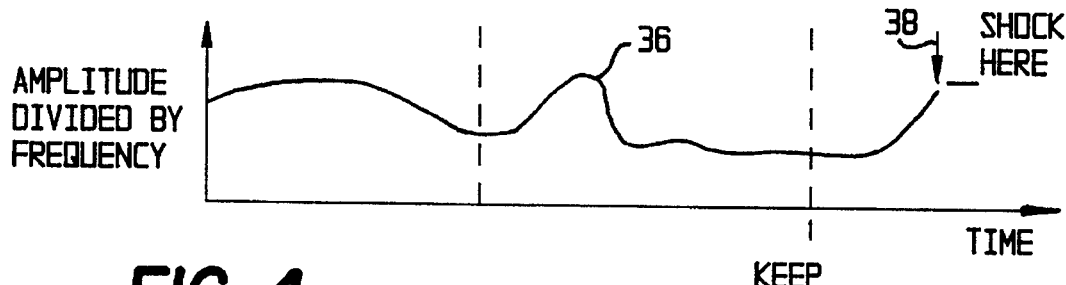
FIG. 4

CARDIOVERTER/DEFIBRILLATOR SHOCK TIMING FUNCTION

BACKGROUND OF THE INVENTION

The present invention relates generally to implantable medical devices, and more particularly to an implantable cardioverter/defibrillator device which provides improved efficiency and energy conservation by delivering a defibrillating shock waveform at the optimum time to a patient's heart in fibrillation. The invention further relates to techniques for more reliable and reproducible determination of the minimum energy requirements for defibrillation.

The importance of speed and effectiveness in reviving/ resuscitating/defibrillating a patient whose heart is in fibrillation cannot be overemphasized. Implantable cardioverters/ defibrillators have the capability to automatically detect abnormal heart rhythm or rate as it occurs and to respond with virtually immediate delivery of an appropriate preselected therapy. Detection of abnormal tachycardia or of fibrillation by the device is initiates automatic delivery of an electrical shock waveform (or, as sometimes termed in this specification, simply "shock") to cardiovert or defibrillate the patient's heart.

Because such devices are battery operated, it is, of course, essential that energy be conserved so that a sufficient amount is available for defibrillation or other available therapy each time it is required by the patient as detected by the device. The condition of the device, including its battery level, is checked periodically by the patient's cardiologist during scheduled visits, but if undesired factors are present it is possible that the battery may nevertheless become depleted or fall to a level insufficient to meet demand for therapy during a cardiac event that occurs before the problem can be discovered at the doctor's office. For a patient whose heart is prone to fibrillation, such a circumstance can prove to be fatal. At the very least, these circumstances will necessitate surgery at more frequent intervals for device replacement.

To conserve energy in the implantable cardioverter/ defibrillator, improved techniques have been developed to avoid device operations that are wasteful of energy, such as false shocking, i.e., delivery of a shock in response to a false detection of tachycardia or fibrillation, or committed operation, in which, once capacitor charging is commenced, a shock will be delivered despite that fibrillation may have spontaneously ceased in the interim. The improvements in energy conservation include better discrimination of cardiac events which require shocking the heart from those events which do not suck treatment. To that end, devices have been implemented with improved detection criteria, and with uncommitted high energy shock therapy so that if, for example, a tachycardia or fibrillation terminates spontaneously, the otherwise inexorable movement toward delivery of a shock is interrupted at that point despite the fact that charging of the device capacitors may have commenced.

Despite such advances, it is essential that when a shock is determined to be appropriate to the patient's cardiac condition, it is delivered at a time when it is most likely to successfully terminate the dysrhythmia and return the heart to normal sinus rhythm. Further, the optimum time should coincide with a point of greatest likelihood that the minimum energy required is delivered to achieve that result, i.e., that the shock is applied when the defibrillation threshold is likely to be lowest. Without such timing, the device may still be depleted of energy prematurely as a result of either the need for delivery of multiple shocks to terminate the episode, or of a single shock which is of higher energy than absolutely necessary because it is applied at a time of high DFT.

U.S. Pat. No. (USPN) 4,384,585 to Zipes describes synchronous cardioversion with the possibility of inducing fibrillation by non-synchronous shocking. In that patent disclosure, it is stated that synchronous cardioversion delivers the shock at a time when the bulk of the cardiac tissue is already depolarized and is in a refractory state, whereas non-synchronous cardioversion is avoided to preclude delivery of cardioverting energy during the vulnerable T-wave portion of the cardiac cycle. Electrogram information from the patient's heart is used to detect depolarizations of the cardiac tissue and to produce a corresponding sense signal. Detection criteria are applied with respect to the sense signal to determine whether a tachyrhythmia is present.

In the '585 patent device as described, the detection circuitry determines the time interval between successive cardiac depolarizations, and initiates a discharge of energy stored in an output storage capacitor if either the average detected heart rate is above a preset threshold for a limited period of time or if the detected heart rate accelerates by a preset amount. Alternatively, the criteria imposed involve detection of a departure of selected beats from a historic data base of a succession of R—R intervals stored in memory; or a waveform analysis of the electrogram information with pattern recognition of time domain or frequency domain characteristics of the tachyrhythmia signal. The shock is delivered in synchrony with the R-wave to avoid a manifest ventricular response.

In U.S. Pat. No. 4,996,984 to Sweeney, a defibrillation method is described in which fibrillation cycle length— constituting the average time interval between successive depolarizations—is measured and stimulation is applied to the heart in the form of multiple bursts of electrical current timed according to that cycle length. As that patent specification points out, when cells of cardiac tissue are activated, the normal electrical polarization represented by the voltage difference within and outside the cell collapses, or depolarizes. Repolarization of the cell then commences, in which this voltage difference is reestablished. Before the repolarization process is completed the tissue is refractory, and afterward it becomes non-refractory—the period from depolarization to non-refractoriness being termed the refractory period. The depolarization activity propagates through the heart, as cells are activated by the collapsing polarization (i.e., depolarization) of adjacent cells.

The '984 patent disclosure teaches that the multiple burst defibrillation technique is optimized by timing the successive bursts to occur at successive depolarizations at a particular site in the myocardium. Thus, the time interval between bursts is adjusted to correspond to the cycle length, to the extent it is feasible to do so. Fibrillation cycle length is determined, according to the patent, by methods such as cross-correlation, auto-correlation, fast Fourier transformation, counting the R-waves of the electrocardiogram over a fixed time period and determining the R—R intervals of individual cardiograms.

In U.S. Pat. No. 5,275,621 to Mehra, a cardioverter device is disclosed which employs a pair of electrodes, one for measuring a near field and the other for measuring a far field, and for developing corresponding near field and far field signals. A cardioversion pulse is delivered in synchrony with detection of the near field signal following detection of onset of the far field signal, using a pair of time intervals measured from onset of the far field signal. Despite a lengthy specification, the '621 patent appears to provide little insight into the significance of these fields, particularly as applied to a scheme for cardioversion.

It has been found that delivery of a cardioverting or defibrillating shock or other stimulating waveform according to teachings presented in the prior art does not result in the optimum time for delivery or in high reproducibility of success. All to often, the prior art proposals lead to triggering the shock at a time of relatively high defibrillation threshold (DFT). This presents a need for large devices, along with a greater likelihood that considerable energy may be wasted each time a shock is delivered, resulting in acceleration of battery depletion, and most significant, a lower likelihood of success in terminating the fibrillation.

It is a principal object of the present invention to provide an improved implantable cardioverter/defibrillator in which detection is such that it enables optimum timing of delivery of the prescribed electrical therapy to a patient's heart, with high reproducibility of performance.

Another object of the invention is to provide a method for reducing the level of energy required to be delivered from an implanted cardioverter/defibrillator to terminate a detected abnormal cardiac event, by optimum timing of the delivery.

A major aspect of the invention is the decrease in defibrillation energy requirements which allows the use of small and lightweight defibrillators.

SUMMARY OF THE INVENTION

The invention is directed toward timing the delivery of electrical cardioverting or defibrillating therapy to a patient's heart from an implanted defibrillator to optimize successful termination of a dysrhythmia in a most effective and energy efficient manner, and in the shortest possible time, to return the patient's heart to normal sinus rhythm. The same principles are applicable where the therapies of cardioversion and defibrillation are available in implantable medical devices having other functions as well, such as a capability to deliver cardiac pacing treatment to the patient.

The invention takes advantage of the observable changes that occur in the cardiac activity characteristics when a human subject's heart is fibrillating. Specifically, changes can be seen in the amplitude and frequency characteristics of the signal from the ECG, whether of the intracardiac, the transthoracic, or the surface type. Studies conducted by the applicants have shown that, in contrast to the prior general assumption in the medical community, the intracardiac discrete ECG signal detected from the intracardiac electrodes represents the status of excitability or nonexcitability of major parts of the heart. Even if the cardiac activity has undergone several fibrillatory cycles, there is always a major fibrillation wavefront that drives these muscular masses through the regular cellular cycle of depolarization and repolarization. Hence, different masses have a status of absolute refractoriness, relative refractoriness and full excitability. Heretofore, it was known that this kind of excitability gap would exist for ventricular tachycardias, but no corresponding body of knowledge existed with respect to ventricular fibrillation. This is a very significant finding, in that the cycle followed by cells of a mass of tissue of the heart during fibrillation or closely related cardiac activity, such as accelerating pathologic tachycardia or flutter, can be used to define or identify a point in the fibrillation cycle at which the heart (ventricular or atrial chambers) is most receptive or susceptible to a defibrillating shock to terminate the fibrillation and revert to sinus rhythm.

The present invention is based on a recognition, then, that when a patient is experiencing fibrillation the amplitude and frequency of the intrinsic ECG signal undergo change with certain characteristic indicia that are detectable from the ECG wave envelope, such as from the intracardiac ECG, attributable to this major fibrillation wavefront and the concomitant regular cellular cycle. According to the invention, the defibrillating shock is timed to be applied in synchronism with (i.e., at or near a point in time at which) the amplitude of the ECG signal when greatest and the frequency of occurrence of discrete intracardiac potentials is the lowest. This point coincides with the time when the heart when the DFT is lowest, which means that successful termination is likely with a relatively small packet of energy.

In a preferred embodiment of the invention, the detection criteria for fibrillation or for acceleration of tachycardia are first assessed by the implanted device to determine whether fibrillation or a substantial likelihood of imminent acceleration into fibrillation is present. If these criteria are fulfilled, a device-implemented command is given to charge its output storage capacitor(s). At that moment and continuing throughout the charging time, the phasic variations in amplitude and frequency of the fibrillation ECG are studied for recognition of a pattern of the phasic variations for timing the delivery. In particular, the pattern sought to be detected is a sufficient number of successive intervals of high amplitude, low frequency cardiac activity to demonstrate a trend from which it can be determined that delivery of the shock should be triggered at the very next interval of increasing amplitude. The desire is to synchronize the delivery of the shock with the detection of a high amplitude and discrete intracardiac ECG potential.

The device may be implemented such that during the time it is assessing whether the basic detection criteria are satisfied, it is also observing the phasic pattern of the intrinsic ECG signal. In any event, the comparative data attributable to fibrillation, which is to be analyzed to time the delivery of a shock, is stored in an internal memory of the device. If the detection criteria are satisfied to establish that accelerating tachycardia or fibrillation is occurring, capacitor charging is commenced. As the charging continues to the desired level—a process that typically takes several seconds—the device is analyzing the trend from the stored historical data and/or from a search period begun with the commencement of charging. Delivery of the shock is initiated at a point of increasing amplitude of the intrinsic ECG signal and of decreasing frequency of occurrence of intracardiac discrete ECG depolarizations in the very next successive interval following the search period, but at a time prior to the end of the search period.

The frequency and amplitude of these events are important, so that the scheme implemented by the invention provides the capability to identify this trend in the intrinsic ECG signal. The factors of interest which identify the significant amplitude and frequency characteristics can be expected to recur for several consecutive intervals of time, and it is highly desirable to screen or scan a large number of events over a search period whose length is sufficient to provide or project the data to determine the point representing the optimum time for delivery of the shock.

The preferred embodiment of the invention employs an interval timer and a peak detector, for ongoing tracking of the intrinsic ECG signal to provide this large data base to enhance the likelihood of optimum timing of the shock. So the search period may run for, say, from one second to eight seconds—the latter being typical of the maximum time to charge the output storage capacitor(s) of the device to the level required for the shock. Each interval of time examined during the search period may occupy from only a few milliseconds to up to one second, depending on the number of cycles which are programmed to be studied in each interval to detect amplitude. The shock is delivered in that interval in which, based on the trend, the intracardiac ECG has the highest amplitude. For example, a one second search period might allow examination and comparison of six consecutive intervals and amplitudes, which constitutes 6 Hertz (Hz).

The scheme determines whether either or both of the amplitude of the intrinsic ECG signal and the interval between occurrences (i.e., reciprocal of frequency) of intracardiac discrete ECG depolarizations are increasing. If both of these parameters are increasing (or even if only one of the two is increasing, but is doing so significantly), then a shock is delivered at a point in the next interval of the search period at which the amplitude is deemed to be greatest. Preferably, the quotient of amplitude divided by frequency is calculated to ascertain optimum timing. To that end, the timer is started at least when the detection criteria have established that fibrillation is present, and a search is conducted, using the peak detector, for T-max over a predetermined search period of, say, 3 or 4 seconds. The search time should be sufficiently long to allow recognition of a trend and identification of the next point of greatest or at least increasing amplitude before the period expires, and yet sufficiently short to avoid missing an early opportunity to terminate the dysrhythmia.

It is therefore another broad object of the invention to provide an implantable device for treating cardiac rhythm disorders, such as atrial or ventricular tachycardia or fibrillation, in which the device includes means for detecting the dysrhythmia of interest, and means responsive to such detection for then searching for the occurrence of events meeting predetermined criteria for the optimum timing of delivery of therapy to achieve the most effective and energy efficient return to sinus rhythm.

Another important object is to provide an implantable defibrillator with the capability for controlling delivery of therapy to coincide with recognition of the point in the fibrillation episode at which the defibrillation threshold is likely to be lowest.

Yet another object of the invention is to provide a defibrillator which times the delivery of an electrical shock to the heart to coincide as closely as possible with the lowest frequency occurrence of intracardiac discrete ECG depolarizations and the highest amplitude portion of the fibrillation ECG signal.

A principal aim of the invention is to achieve optimum performance from an implantable cardioverter/defibrillator, with high reproducibility or repeatability.

BRIEF DESCRIPTION OF THE DRAWINGS

The above and other objects, aspects, features and attendant advantages of the invention will be recognized from the following detailed description of a preferred embodiment and method constituting the presently considered best mode of practicing the invention, in conjunction with the accompanying drawings, in which:

FIG. 1 is a schematic representation of the heart showing tissue with small and large reentry loops for pathologic tachycardia and fibrillation;

FIG. 3 is a representation of the ECG signal, showing various stages of tachycardia and fibrillation with determination of timing of delivery of a shock according to principles and criteria implemented in prior art devices;

FIG. 4 is a representation of amplitude divided by frequency for the ECG of FIG. 3, to illustrate the principles and criteria employed in a device to recognize and treat fibrillation according to the present invention;

DESCRIPTION OF THE PREFERRED EMBODIMENT AND METHOD

Figure 2:
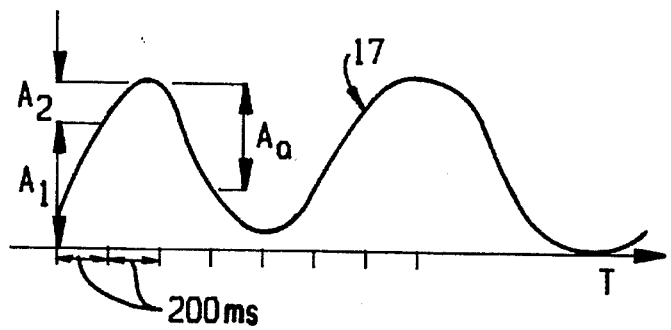
FIG. 2 is a graph of a signal waveform showing the use of preselected time interval windows for recognizing frequency and amplitude of signal components in various frequency ranges.

This optimum timing of the application of a shock is based on the factors affecting or producing the amplitude and frequency of the ECG of the fibrillating heart. Reentry mechanisms in the larger circuit loops of the heart tissue exhibit higher amplitude than those in the smaller reentry loops, since more muscle is involved in the former than in the latter. Also, a lower frequency is exhibited because a greater time period is required for a given wavefront with a given speed to complete the larger loop.

Viewed somewhat differently, and with reference to FIG. 1, larger reentry loops 10 and smaller reentry loops 13 exist in the tissue of a heart 15 in fibrillation. The larger loops 10 have lower frequencies and higher amplitudes, whereas the smaller loops 13 have higher frequencies and lower amplitudes. It is relatively easier to reset the small loops by depolarizing some areas to stop those loops from circulating, thereby making use of the already depolarized large group of muscles. Therefore, the shock should be timed to fall within the absolute refractory period of the highest amplitude ECG signal. This makes use of the fact that a majority of the heart is already in an excitable status and that there is a need for the shock energy delivered to depolarize and reset only smaller muscular masses. Aside from many other factors, since the energy needed for defibrillation directly depends on how much excitable muscular tissue needs a minimum field gradient to be depolarized, the defibrillation energy requirements are lower the less muscular mass is involved in the critical resetting. If a shock is timed within the relative excitability of a larger muscle group—indicated by the intracardiac signal—the probability is that another reentry circuit will be induced in the depolarization process. These reemerging reentry loops will cause a return to the chaotic cardiac activity—fibrillation—or will simply maintain the fibrillation. Less effort (energy) is needed to break the coarse and high amplitude, low frequency circuit movements than the small ones.

The correlation between the waveform that travels through the heart in these circuits and the tachycardia movements in the ECG, is that a larger mass of the muscle of the heart is involved in the larger loop and therefore the amplitude of the ECG signal is greater. In contrast, if the fibrillation concerns only small areas of circulation, then the amplitude is smaller and the frequency is higher.

The preferred technique to discriminate the optimum time during fibrillation for delivery of a defibrillating shock considers both the amplitude and the frequency (or interval)

of the intrinsic ECG signal. Moreover, by triggering the shock for delivery to the patient's heart based on a discrimination factor of the quotient of the amplitude and the frequency (or interval) of the ECG, a better indication is obtained. The frequency may be observed by filtering. One may look at different bands in a window—say, from 3–5, 5–7, 7–9, and 9–11 Hz, for example, to determine the frequency content. Zero crossings and integral delta modulation, or alternatively, peak detection, of the signal will serve to determine the amplitude in those frequency bands.

In general, the device operates to recognize a dysrhythmia, specifically pathologic tachycardia or fibrillation, by use of known, conventionally applied internal detection criteria. When these criteria are fulfilled, the device looks at whether the cardiac signal indicates ongoing tachycardia or fibrillation, and ultimately, whether sinus rhythm is restored. If the criteria for fibrillation are satisfied, the device immediately initiates charging of its shocking capacitor(s). During the several seconds of time required to charge the capacitor(s) to an energy level needed to break the fibrillation, the device continues to check the occurrence of phasic variations in amplitude and frequency of the ECG. Then, it delivers the shock at a time when it detects the existence of the highest amplitude and lowest frequency of the fibrillation ECG, or as nearly as that can be determined, which is when the greatest probability of successful defibrillation exists.

Of course, it is not possible to predict with unerring certainty the precise moment at which the highest amplitude will occur. Instead, the device detects relative frequency and amplitude to identify a trend, and makes a decision on timing the delivery of a shock based on the increasing amplitude and decreasing frequency of the cardiac activity over at least several successive predetermined time intervals or "windows".

First, the general criteria must be met that this is fibrillation, and then the charging starts. During that charging time, the device will be seeking to optimize timing of the shock delivery. Pattern recognition may be and preferably is used to identify the occurrence of highest amplitude and lowest frequency, and is commenced at the moment fibrillation is detected. To fulfill the timing criteria, a multiplicity of events of this type, perhaps a dozen or more, may be required to establish the diagnosis. In that time, the device is looking at the phasic pattern of the ECG, and an internal memory is used for storage of the data for the comparison.

Detection may be performed by filtering. For example, the device can be implemented to look at the amplitude of the ECG within a certain short interval of time, to obtain the maximum amplitude that occurs within that time window. Referring to FIG. 2, if it is assumed that a 200 millisecond (ms) window is monitored to locate the minimum and maximum points, then any signal can be found up to a maximum of five Hz. In the first 200 ms interval of waveform or signal 17, the amplitude between the minimum and the maximum for that interval is $A_1$. In the second interval the amplitude is $A_2$; and in the third interval the amplitude is $A_3$. On the other hand, anything above 5 Hz will not allow detection of all the maximums and minimums because several could occur in a single window or interval. Calling up different windows will allow observations to be made as necessary or desired. For example, a 100 ms window allows observations to be made up to the 10 Hz range. This provides a means to handle both amplitude and frequency together.

With reference to FIG. 3, the course of the ECG 21 is sinus rhythm 22, and suddenly a tachycardia 23 commences. It gets faster, and then goes into a chaotic state 27, recovers slightly, and then has some very rapid beats, and reverts again to fibrillation 28. As indicated in the Figure, the device begins looking for fibrillation at 30 when the ECG indicates a tachycardia is commencing. When the fibrillation criteria are fulfilled, at 32, the logic indicates that the heart is in fibrillation, and the command is given, at 33, to charge the capacitor.

A full charge takes a certain time interval that depends on the energy required and the type and size of the capacitor(s) involved. Typically, the charging interval is five to eight seconds. Conventionally, a recheck is made by the implanted device during the charging interval to ascertain a status of ongoing fibrillation. In the prior art devices, if the recheck indicated continuing fibrillation the device would simply issue a command, at 35, to deliver the shock, as much as possible in synchronism with the R-wave. If the recheck indicated an absence of fibrillation or accelerating tachycardia, the charging was interrupted and/or delivery of the shock was aborted.

According to the present invention, however, if the recheck shows ongoing fibrillation, the device commences a further operation to observe and compare periodic variations in amplitude and frequency, preferably calculating the quotient of amplitude divided by frequency as shown in FIG. 4, on the same time scale as the ECG illustrated in FIG. 3. When a trend of successive intervals of increasing amplitude and decreasing frequency of the intrinsic ECG signal is detected, such as at 36, the device triggers the delivery of a shock, at 38, in the next interval of increasing amplitude, synchronized with T-max, a point of low DFT.

Factors that influence DFT include the pulse characteristics of shock waveform and shock duration, and the electrode characteristics of lead configuration and lead material. Normally, the amplitude of the fibrillation in the ECG signal is 20 to 60% of the sinus signal. The desire is to continue searching after the recheck of fibrillation comes back in the affirmative, to find the optimum time at which the criteria of high value of amplitude divided by frequency is fulfilled. At some point in time, it reaches a level that exceeds the one seen earlier, but at least about the same as the earlier level. This means the timing-of-delivery criteria are fulfilled, or the search time is over, and consequently the shock is delivered at that moment. Compared with a shock delivered by a conventional device that uses a simple one recheck criterion, 20%+less energy is required to break the fibrillation, on average, and a 20 to 30% higher probability exists that the shock will be effective and successful in terminating the fibrillation.

Figure 5:
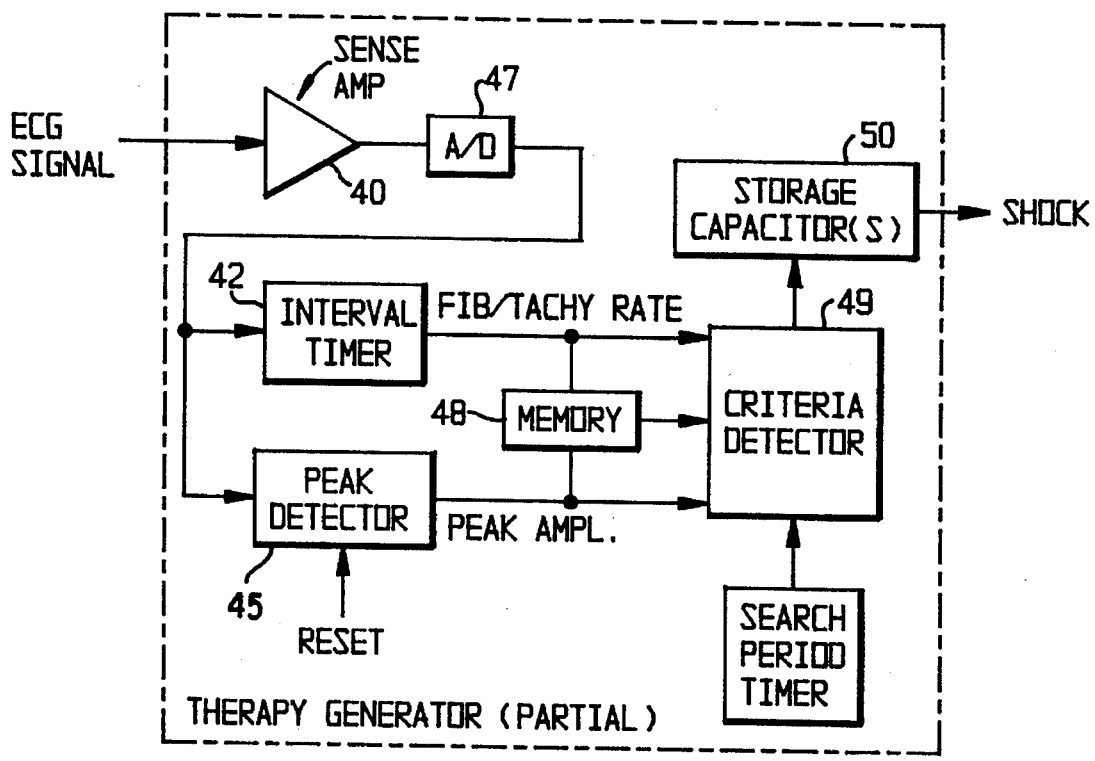
FIG. 5 as a simplified block diagram of an automatic implantable cardioverter/defibrillator which incorporates the principles of the present invention to defibrillate the ventricle or atrium of the human heart.

Referring now to FIG. 5, a presently preferred embodiment of the invention includes a therapy generator having a sense amplifier 40 coupled to receive an intracardiac intrinsic ECG signal, which is digitized by an analog-to-digital (A/D) converter 47. The sense amplifier performs ongoing tracking of the intrinsic ECG signal for application of detection criteria to determine whether any of accelerating pathologic tachycardia, flutter, or fibrillation is occurring in the heart chamber being monitored. The digitized detection output is supplied to each of an interval timer 42 and a peak detector 45. The historical data may be stored in an internal memory 48 to provide a data base of the heart rate of the detected dysrhythmia over a timed search period with interval settings, determined by the interval timer.

Preferably, the search period is programmable to encompass a multiplicity of desired intervals ranging in total to from one second to ten seconds. The search period should be extensible beyond the time required to fully charge the output storage capacitor(s) 50 of the implanted medical interventional device to the level required for the shock to be used for cardioversion or defibrillation, depending on the nature of the particular detected dysrhythmia. In the case of fibrillation, actual or impending (based on the behavior of, say, an accelerating pathologic tachycardia), the charging time required to develop the level of charge for the defibrillation shock waveform may, for example, be in the range from seven to eight seconds. The search is conducted to identify the optimum time for delivery of the shock, and such identification should be constrained to be made so that delivery will take place as soon after the search period expires as the specified characteristics of the ECG signal are predicted or projected to occur.

Each of a plurality of equal time intervals in a sequence constituting the search period is examined to denote the point on the intracardiac ECG of optimum timing for delivery of the shock. Each such time interval may occupy on the order of, say, 200 ms to one second, depending on the number of cycles (or portion of a cycle) of the intrinsic ECG signal to be examined in each interval to detect peak amplitude. The shock is ultimately to be delivered at the precise point in time in that interval when, based on the historical trend gleaned from the stored data, the intracardiac ECG has the highest amplitude (or is increasing toward that amplitude) and the frequency of intracardiac discrete ECG depolarizations is lowest (or is decreasing, which represents a trend toward increasing value of the interval between such polarizations). A one second search period would allow examination and comparison of five consecutive intervals (of 200 ms each) and peak amplitudes, constituting 5 Hz of the signal.

If both amplitude and interval between occurrences of depolarizations the intrinsic ECG signal are increasing, the energy stored in the capacitor(s) is automatically released in a predetermined shock waveform configured by the implanted device and delivered at a point in the search period at which the amplitude is either at or projected to be the greatest (the optimum time). Triggering of this automatic action is accomplished by a discharge command to the energy storage capacitor section of the device from shock timing criteria detector 49. The device is readily implemented to deliver the shock at the optimum time even if only one of the two parameters is increasing.

In the preferred embodiment, the quotient of intracardiac ECG signal amplitude divided by frequency of discrete polarizations, obtained in the course of the search, is calculated to ascertain optimum timing. Here also, the search period may be commenced when the basic detection criteria of the sense amplifier have established that fibrillation is present. The search is conducted for T-max over a predetermined search period of, say, 3 or 4 seconds. In each case, the search period should occupy a time interval sufficiently long to allow recognition of a trend and projection of the next point of greatest or at least increasing signal amplitude before the period expires, and yet a time interval sufficiently short to avoid missing an early opportunity to terminate the dysrhythmia.

Figure 6:
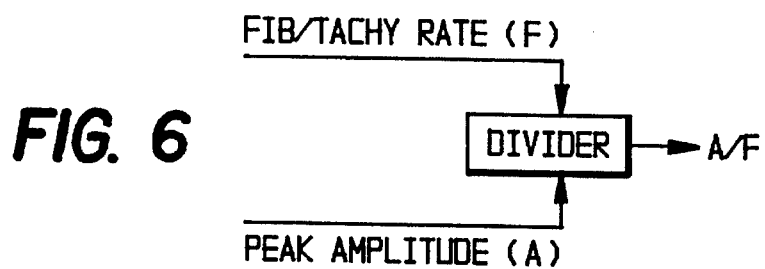
FIG. 6 is an alternative embodiment of a portion of the device of FIG. 5.

Referring now to FIG. 6, an alternative to using the two separate indicia of rate (frequency, or its reciprocal, interval) and amplitude as the shock timing criteria, is to use a single indicia representing the quotient of ECG signal amplitude and frequency, as in the chart of FIG. 4. In this case, the shock timing criterion is calculated by a divider having inputs of peak amplitude and frequency.

The foregoing principles are particularly advantageous for implementing ventricular defibrillation. For atrial defibrillation, measurement of the intrinsic signal's interval from P' to P' in the atrium is helpful to identify the shock timing as well. The only difference for the purpose of optimum timing of shock delivery to achieve atrial defibrillation, aside from processing the intrinsic atrial ECG signal, involves also measuring the R waves to synchronize the defibfillation shock. The shock synchronization is to the highest atrial amplitude at lowest frequency, and also to the R wave to prevent ventricular fibrillation following non-synchronized atrial shocks.

Although certain preferred embodiments and methods have been disclosed herein, it will be appreciated that those skilled in the art to which the invention pertains will recognize variations and modifications from a consideration of the foregoing description, without departing from the spirit and scope of the invention. Accordingly, it is intended that the invention shall be limited only as required by the appended claims and the rules and principles of applicable law.

What is claimed is:

1. An implantable defibrillator for automatic timing of shock wave therapy in response to sensing an intracardiac intrinsic ECG signal of the patient's heart indicative of fibrillation, comprising:

therapy delivery means responsive to detection of fibrillation for developing a prescribed electrical shock waveform therapy to be applied to the heart to terminate the fibrillation for reversion of the heart to sinus rhythm, detection means for detecting fibrillation from a predetermined set of detection criteria, and timing function means further responsive to detection of fibrillation and observation of a fibrillation cycle of the intrinsic ECG signal for timing delivery of said shock waveform therapy to the heart at a point in time in said fibrillation cycle which is synchronous with a sensed intracardiac potential of substantially highest amplitude and relatively low frequency of occurrence of sensed discrete intracardiac events in the intrinsic ECG signal, said sensed intracardiac potential being selected from a multiplicity of intracardiac sensed events in said fibrillation cycle of the intrinsic ECG signal, whereby to enhance the probability of successful termination of the fibrillation at a low energy level of said shock waveform therapy.

2. The device of claim 1, in which:

said timing function means is further responsive to detection of fibrillation and observation of the fibrillation cycle for timing said delivery at a point in time synchronous with substantially the lowest frequency of occurrence of sensed discrete intracardiac potentials of substantially lowest frequency selected from said multiplicity of intracardiac sensed events in the intrinsic ECG signal.

3. The device of claim 1, in which:

said timing function means includes means for establishing said multiplicity of intracardiac sensed events in a corresponding multiplicity of equal time intervals of said intracardiac signal.

4. The device of claim 1, in which:

said timing function means includes means for selecting said sensed intracardiac potential from a multiplicity of intracardiac sensed events in said intrinsic ECG signal.

5. The device of claim 3, in which:

the dysrhythmia under treatment is fibrillation, said developed prescribed electrical waveform regimen is a shock waveform, and said timing function means includes means for dividing the amplitude of each of said intracardiac sensed events by the frequency content of said intrinsic ECG signal thereat to aid in sensing said intracardiac potential of substantially highest amplitude in tracking said multiplicity of intracardiac sensed events.

6. A method for optimally timing the automatic delivery of an appropriate therapy from an implantable cardioverter/defibrillator device adapted to be implanted in a patient, in response to sensing an intracardiac intrinsic ECG signal of the patient's heart indicative of fibrillation, said method comprising the device-implemented steps of:

detecting fibrillation from a predetermined set of detection criteria, and if fibrillation is detected, observing whether amplitude and interval between occurrences of depolarizations in successive fibrillation cycles of the intrinsic ECG signal are increasing, developing an electrical shock waveform in response to detection of fibrillation, as an electrical therapy to be applied to the heart to terminate the fibrillation and for reversion of the heart to sinus rhythm, further responding to detection of fibrillation and said observation of whether amplitude and interval between occurrences of depolarizations in successive fibrillation cycles are increasing by selecting at least one of a sensed intracardiac potential of substantially highest amplitude in the intrinsic ECG signal and a substantially greatest of said interval between occurrences of depolarizations, from a multiplicity of intracardiac sensed events in said intrinsic ECG signal, and timing delivery of the developed prescribed electrical waveform regimen to the heart at a point in time synchronous with said selected at least one of said sensed intracardiac potential of substantially highest amplitude and said substantially greatest interval, whereby to enhance the probability of successful termination of said fibrillation at a low energy level of said electrical shock waveform with reproducibility of such success for subsequent episodes of fibrillation.

7. The method of claim 6, wherein said timing of said delivery is selected to be at a point in time synchronous with frequency of occurrence of sensed discrete intracardiac potentials of substantially lowest frequency selected from said multiplicity of intracardiac sensed events in the intrinsic ECG signal.

8. The method of claim 6, wherein:

said timing of said delivery is selected to be synchronous with both of substantially the highest amplitude and substantially the lowest frequency of sensed discrete intracardiac potentials selected from said multiplicity of intracardiac sensed events in the intrinsic ECG signal.

9. The method of claim 6, further including:

dividing the amplitude of each of said intracardiac sensed events by the frequency of occurrence of sensed discrete intracardiac potentials of substantially lowest frequency selected from said multiplicity of intracardiac sensed events in the intrinsic ECG signal to aid in sensing said intracardiac potential of substantially highest amplitude in tracking said multiplicity of intracardiac sensed events.

10. A method of optimum timing of the delivery of a therapeutic electrical shock to the heart of a patient in which a shock delivery device is implanted, in response to detection by the device of actual or imminent ongoing ventricular fibrillation of the patient's heart, said method comprising:

monitoring the intracardiac ECG potential, and triggering the delivery of a shock to the ventricles synchronously with a sensed intracardiac potential of highest amplitude and substantially lowest frequency following a plurality of cycles of sensed intracardiac events of increasing amplitude in the monitored intracardiac ECG potential, while avoiding shock delivery in a relative refractory period of tissue cells of the heart contributing to said sensed intracardiac event of highest amplitude, to achieve reproducible, low shock energy defibrillation of the ventricles.

11. An implantable cardioverter/defibrillator device adapted to be implanted in a patient for automatic initiation of therapy in response to sensing an intracardiac intrinsic ECG signal of the patient's heart indicative of fibrillation, comprising:

therapy delivery means responsive to detection of fibrillation for developing an electrical shock waveform to be applied to the heart to terminate the fibrillation, detection means for detecting said fibrillation from a predetermined set of detection criteria and for observing a fibrillation cycle associated therewith, and timing function means further responsive to detection of fibrillation and observation of the fibrillation cycle for timing delivery of the developed electrical shock waveform to the heart at a point in time in said fibrillation cycle which is synchronous with a sensed intracardiac potential of substantially highest amplitude selected from a multiplicity of said intracardiac sensed events in the fibrillation cycle of the intrinsic ECG signal, whereby to enhance the probability of successful termination of said fibrillation at a low energy level of said electrical shock waveform with reproducibility of such success for subsequent episodes of fibrillation, said timing function means including means for establishing said multiplicity of intracardiac sensed events in a corresponding multiplicity of equal time intervals of said intracardiac signal, and means for dividing the amplitude of each of said intracardiac sensed events by the frequency content of said intrinsic ECG signal thereat to aid in sensing said intracardiac potential of substantially highest amplitude in tracking said multiplicity of intracardiac sensed events.

* * * * *